(12) United States Patent
Qiu

(10) Patent No.: US 9,975,834 B2
(45) Date of Patent: May 22, 2018

(54) POLYFLUOROALKYLATED ALKENES AND SILICON COMPOUNDS PREPARED THEREFROM

(71) Applicant: 3M INNOVATIVE PROPERTIES COMPANY, St. Paul, MN (US)

(72) Inventor: Zai-Ming Qiu, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days. days.

(21) Appl. No.: 15/324,741

(22) PCT Filed: Aug. 11, 2015

(86) PCT No.: PCT/US2015/044572
§ 371 (c)(1),
(2) Date: Jan. 9, 2017

(87) PCT Pub. No.: WO2016/032739
PCT Pub. Date: Mar. 3, 2016

(65) Prior Publication Data
US 2017/0197896 A1    Jul. 13, 2017

Related U.S. Application Data

(60) Provisional application No. 62/042,482, filed on Aug. 27, 2014.

(51) Int. Cl.
*C07C 43/00* (2006.01)
*C07C 43/17* (2006.01)

(52) U.S. Cl.
CPC .................................. *C07C 43/17* (2013.01)

(58) Field of Classification Search
None
See application file for complete search history.

(56) References Cited

U.S. PATENT DOCUMENTS

| | | |
|---|---|---|
| 3,159,662 A | 12/1964 | Ashby |
| 3,178,464 A | 4/1965 | Pierpoint |
| 3,220,972 A | 11/1965 | Lamoreaux |
| 3,313,773 A | 4/1967 | Lamoreaux |
| 3,410,886 A | 11/1968 | Joy |
| 3,470,225 A | 9/1969 | Knorre |
| 3,567,755 A | 3/1971 | Seyfried |
| 3,715,334 A | 2/1973 | Karstedt |
| 3,775,452 A | 11/1973 | Karstedt |
| 3,814,730 A | 6/1974 | Karstedt |
| 3,814,731 A | 6/1974 | Nitzsche |
| 4,276,252 A | 6/1981 | Kreis |
| 4,288,345 A | 9/1981 | Ashby |
| 4,510,094 A | 4/1985 | Drahnak |
| 4,530,879 A | 7/1985 | Drahnak |
| 4,603,215 A | 7/1986 | Chandra |
| 4,640,939 A | 2/1987 | Cavezzan |
| 4,670,531 A | 6/1987 | Eckberg |
| 4,699,813 A | 10/1987 | Cavezzan |
| 4,705,765 A | 11/1987 | Lewis |
| 4,712,092 A | 12/1987 | Bodridge, Jr. |
| 4,916,169 A | 4/1990 | Boardman |
| 5,126,394 A | 6/1992 | Revis |
| 5,159,527 A | 10/1992 | Flynn |
| 5,286,815 A | 2/1994 | Leir |
| 5,639,845 A | 6/1997 | Inomata |
| 5,648,407 A | 7/1997 | Goetz |
| 5,677,050 A | 10/1997 | Bilkadi |
| 5,688,884 A | 11/1997 | Baker |
| 6,129,980 A | 10/2000 | Tsukada |
| 6,255,536 B1 | 7/2001 | Worm |
| 6,299,799 B1 | 10/2001 | Craig |
| 6,329,058 B1 | 12/2001 | Arney |
| 6,353,037 B1 | 3/2002 | Thunhorst |
| 6,376,569 B1 | 4/2002 | Oxman |
| 6,462,100 B1 | 10/2002 | Thunhorst |
| 6,482,979 B1 | 11/2002 | Hintzer |
| 7,279,210 B2 | 10/2007 | Hulteen |
| 8,003,004 B2 | 8/2011 | Bulinski |
| 8,193,393 B2 | 6/2012 | Flynn |
| 8,261,560 B2 | 9/2012 | Flynn |
| 8,591,761 B2 | 11/2013 | Flynn |
| 2005/0046595 A1 | 3/2005 | Blyth |
| 2005/0113609 A1 | 5/2005 | Furukawa |
| 2006/0135673 A1 | 6/2006 | Temperante |
| 2007/0299276 A1 | 12/2007 | Feiring |
| 2010/0324253 A1 | 12/2010 | Ito |
| 2011/0232870 A1 | 9/2011 | Flynn |
| 2012/0157703 A1 | 6/2012 | Marciniec |
| 2012/0280189 A1 | 11/2012 | Warren |
| 2013/0074130 A1 | 3/2013 | Robbins |
| 2013/0292614 A1 | 11/2013 | Tuma |

FOREIGN PATENT DOCUMENTS

| | | |
|---|---|---|
| EP | 0238033 | 9/1987 |
| EP | 0355025 | 2/1990 |
| EP | 0355652 | 2/1990 |
| JP | H01-226844 | 9/1989 |
| WO | 1998-40439 | 9/1998 |
| WO | 2006-007917 | 1/2006 |
| WO | 2013-151741 | 10/2013 |
| WO | 2014-193654 | 12/2014 |
| WO | 2015-050740 | 4/2015 |
| WO | 2015-050928 | 4/2015 |
| WO | 2015-153152 | 10/2015 |
| WO | 2016-032738 | 3/2016 |
| WO | 2016-032794 | 3/2016 |

OTHER PUBLICATIONS

Phillips, "Application of ESCA and Contact Angle Measurements to Studies of Surface Activity in a Fluoropolymer Mixture", Journal of Colloid and Interface Science, Aug. 1976, vol. 56, No. 2, pp. 251-254.

International Search Report for PCT International Application No. PCT/US2015/044572, dated Oct. 14, 2015, 4pgs.

*Primary Examiner* — Ana Z Muresan

(74) *Attorney, Agent, or Firm* — Kent S. Kokko

(57) ABSTRACT

Novel polyfluoroalkylated alkenes compounds prepared therefrom are described.

5 Claims, No Drawings

POLYFLUOROALKYLATED ALKENES AND SILICON COMPOUNDS PREPARED THEREFROM

CROSS REFERENCE TO RELATED APPLICATIONS

This application is a national stage filing under 35 U.S.C. 371 of PCT/US2015/044572, filed Aug. 11, 2015, which claims the benefit of U.S. Application No. 62/042,482, filed Aug. 27, 2014, the disclosure of which is incorporated by reference in its/their entirety herein.

FIELD

This invention relates to methods of treating substrates (especially substrates having a hard surface such as, for example, ceramics or glass) to impart water, oil, stain, and/or dirt repellency to a surface thereof, and, in other aspects, this invention relates to compositions for use in the methods and to substrates treated thereby.

BACKGROUND

Various fluorochemical compositions have been used as coating compositions for application to substrates (for example, hard surface substrates and fibrous substrates) to impart low surface energy characteristics such as oil and/or water repellency (oleophobicity and/or hydrophobicity). When used in coatings or films, however, many fluorochemical materials have tended to diffuse to the surface of the coating or film and to become depleted over time (for example, due to repeated cleanings of the surface). This has led to the use of fluorochemical derivatives having reactive or functional groups (for example, perfluoropolyether thiols, silanes, phosphates, and acrylates) to enable covalent attachment to the coatings, films, or substrate surfaces.

Silane and silicone compounds having one or more fluorochemical groups have been used (alone and in combination with other materials) to prepare surface treatment compositions for substrates such as glass and ceramics. Such silane compounds have typically included one or more hydrolyzable groups and at least one polyfluorinated alkyl or polyether group.

Numerous fluorochemical surface treatments have been developed and have varied in their ease of applicability to substrates (for example, due to differences in viscosity and/or in solvent solubilities, some treatments even requiring expensive vapor deposition or multiple application steps), in their requisite curing conditions (for example, some requiring relatively high curing temperatures for relatively long periods of time), in their repellency levels, in their ease of cleaning, in their degrees of optical clarity, and/or in their durability (for example, in their chemical resistance, abrasion resistance, and/or solvent resistance). Many have also been at least somewhat substrate-specific, requiring production of multiple compositions to ensure adhesion to different substrates.

SUMMARY

There exists an ongoing need for surface treatment processes (and fluorochemical compositions for use therein) that can meet the performance requirements of a variety of different surface treatment applications. Such processes will preferably be simple, cost-effective, compatible with existing manufacturing methods, and/or capable of imparting repellency to a variety of different substrates.

Briefly, in one aspect, this invention provides a novel polyfluoroalkyl alkenes and, derived therefrom, novel fluoroalkylsilicon compounds, including fluoroalkylsilicones and fluoroalkylsilanes. In another aspect this disclosure provides a coating composition comprising the fluoroalkylsilicone compounds with high water repellency, as measure by the receding water contact angle. In another aspect this disclosure provides a process for making the fluoroalkylsilicone compounds. In another aspect, this disclosure provide a surface treatment process which comprises (a) providing at least one substrate having at least one major surface; coating the surface with the coating composition, and curing the coating. In another aspect this disclosure provides the coated articles which have high water contact angles, especially receding water repellency.

The present disclosure provides novel fluoroalkyl silicon compounds that can be used as release materials or can also be blended with one or more additional low surface energy materials (e.g., fluoropolymers, polyacrylates with pendent $R_f$ group, lower cost fluoroalkyl silicones and non-fluorinated silicones) while maintaining the desired low release characteristics of the instant fluorosilicone material. In addition, in some embodiments, high blend ratios of low surface energy materials may be used without detrimentally affecting the re-adhesion force of the adhesive after removal of the blended release materials comprising the present fluoroalkyl silicon compounds.

DETAILED DESCRIPTION

In a first embodiment, the present disclosure provides novel polyfluoroalkyl alkenes of the formula:

$$[R_f\text{—O—CHFCF}_2\text{—O}]_x\text{—R*—CH=CH}_2, \quad \quad \text{I}$$

wherein
$R_f$ is a perfluoroalkyl group, optionally substituted by one or more in-chain —O—, or —$NR_f^1$-heteroatoms, where $R_f^1$ is a perfluoroalkyl;
subscript x is at least two; and
R* is (hetero)hydrocarbyl group of valence x+1, and is preferably selected from C2-C10 alkylene.

The $R_f$ groups may be linear or branched and of the formula:
$C_aF_{2a+1}$—, where a is at least 1, preferably at least 3, more preferably 3-6; or may be have in-chain oxygen as in the formula:
$C_aF_{2a+1}$—(O—$C_bF_{2b}$)$_c$—, where a is at least 1, b is at least 2, and c may be a number from 1 to 10;
or may have in-chain nitrogen as in the formula:
$C_aF_{2a+1}N(C_aF_{2a+1})$—$C_bF_{2b}$—, where each a is at least 1, and b is at least 2. Preferably, each of the perfluoroalkyl or perfluoroalkylene groups are selected from $C_3$-$C_6$.

It has been reported that certain perfluorooctyl-containing compounds ($C_8F_{17}$—) may tend to bio-accumulate in living organisms; this tendency has been cited as a potential concern regarding some fluorochemical compositions. For example, see U.S. Pat. No. 5,688,884 (Baker et al.). As a result, there is a desire for fluorine-containing compositions effective in providing desired functional properties, e.g., water- and oil-repellency, surfactant properties, etc. while eliminating more effectively from biological systems. However, it has also been asserted that only perfluoroalkyl groups of the formula $F(CF_2)_n$— have six or greater carbons have the self-alignment capability to achieve useful performance, while shorter chains, e.g. $C_4F_9$— lack the self-alignment necessary for good performance. See Phillips and Dettree, J. Col and Interface Sci., vol. 56(2), August 1976.

Therefore it remains a challenge to provide shorter chain perfluoroalkyl compositions that are less bioaccumulative, while maintain the requisite performance.

In some preferred embodiments, the present fluoroalkyl-silane compounds and coating compositions provide the necessary performance even with the shorter $C_3$-$C_6$ perfluoroalkyl groups. Furthermore, the short chain perfluorocarboxylic acids (the presumed intermediate degradation products) are less toxic and less bioaccumulative than the longer chain ($C_8$) homologues. For these reasons, the $R_f$ groups is preferably selected from $C_3$-$C_6$ perfluoroalkyl (and/or perfluoroalkylene) groups. The present invention provides novel fluoroalkyl alkenes, having multiple fluoroalkyl groups pendent from the same branch, increasing the fluoroalkyl content, while reducing the chain length thereof.

The fluoroalkyl compounds of Formula I may be prepared by reaction of a compound of the formula:

$$R_f\text{—O—CF}\!=\!\text{CF}_2 \qquad \text{II}$$

with a terminally unsaturated polyol of the formula:

$$(\text{H—O—})_x\text{—R*CH}\!=\!\text{CH}_2, \qquad \text{III}$$

in the presence of a base catalyst as described in US20050113609, and where R*, subscript x and $R_f$ are as previously defined.

The perfluorovinyl ether of Formula II, in turn, may be prepared by fluoride ion catalyzed addition of a perfluorinated acid fluoride to hexafluoropropylene oxide, followed by decarboxylation, according to the techniques describe in U.S. Pat. No. 6,255,536 (Worm et al.), incorporated herein by reference. Perfluorinated acid fluoride may be obtained from hexafluoropropene oxide by reaction with a metal fluoride. Alternatively, the perfluorinated acid fluorides may be prepared by electrochemical fluorination of alcohols, acids or esters as known in the art, for example as described in U.S. Pat. No. 6,482,979 (Hintzer et al.), incorporated herein by reference.

Commercial available perfluorovinyl ethers of Formula II are, for example, $CF_3OCF\!=\!CF_2$, $CF_3CF_2CF_2OCF\!=\!CF_2$ and $CF_3OCF_2CF_2CF_2OCF\!=\!CF_2$.

With reference to Formula III, R* may be any (hetero) hydrocarbyl group, Preferably R* is an alky or aryl group.

The perfluorovinyl ethers of Formula II may be used to prepare polyfluoroalkylated silicon compounds, including silanes and silicones of the general formula $$[R_f\text{—O—CHFCF}_2\text{—O}]_x\text{—R*—Si*}, \qquad \text{IV}$$

wherein
$R_f$ is a perfluoroalkyl group, as previously defined;
R* is (hetero)hydrocarbyl group of valence x+1;
subscript x is at least two; and
Si* is a silane or silicone group.

More particularly, the present disclosure provides fluoroalkyl silanes of the formula:

$$[R_f\text{—O—CHFCF}_2\text{—O}]_x\text{—R*—Si(X)}_q R^2_{3-q}, \qquad \text{V}$$

wherein
$R_f$ is a perfluoroalkyl group, as previously defined;
R* is (hetero)hydrocarbyl group of valence m+1;
subscript x is at least two;
X is a hydrolysable group;
$R^2$ is a $C_1$-$C_4$ alkyl group; and
subscript q is 1 to 3.

The present disclosure also provides fluoroalkyl silicones of the formula:

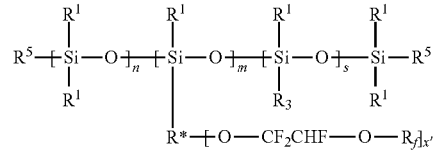

each $R^1$ is independently an alkyl or aryl;
$R_f$ is a perfluoroalkyl group, optionally substituted by one or more in-chain —O—, —S— or —$NR_f^1$— heteroatoms, where $R_f^1$ is a perfluoroalkyl, preferably a $C_1$-$C_6$ perfluoroalkyl;
$R^3$ is —H, —$OR^4$; where $R^4$ is a $C_1$-$C_4$ alkyl
n is 0 to 2000;
m may be zero;
p may be zero,
n+m+p is at least one;
q is at least 3;
$R^5$ is H, alkyl, aryl —R*[—O—$CF_2$CHF—O—$R_f]_x$, or $R^3$;
R* is a (hetero)hydrocarbyl groups of valence x+1;
x is at least 2;
wherein the fluoroalkyl silicone has at least one fluorinated group of the formula —R*[—O—$CF_2$CHF—O—$R_f]_x$.

The silicone compounds of Formula IV is prepared by hydrosilation of a fluorinated compound of the formula:

$$[R_f\text{—O—CHFCF}_2\text{—O}]_x\text{—R*—CH}\!=\!\text{CH}_2, \qquad \text{I}$$

wherein
$R_f$ is a perfluoroalkyl group, as previously described;
subscript x is at least two;
R* is (hetero)hydrocarbyl group of valence m+1,
with a hydrosilane of the formula:

$$\text{H—Si*}, \qquad \text{VII}$$

in the presence of a hydrosilation catalyst, where Si* is a reactive silane or silicone.

More particularly, the fluoroalkyl silanes of formula V may be prepared by hydrosilation with a hydrosilane of the formula:

$$\text{H—Si(X)}_q R^2_{3-q}, \qquad \text{VIII}$$

in the presence of a hydrosilation catalyst, where
X is a hydrolysable group;
$R^2$ is an alkyl group or an aryl group; and
q is 1 to 3.

The X groups can be the same or different and are capable of hydrolyzing, for example, in the presence of water, optionally under acidic or basic conditions, to produce groups capable of undergoing a condensation reaction (for example, hydroxysilyl groups). Desirably, each X is independently selected from hydroxyl, halogen, alkoxy, acyloxy, aryloxy, and combinations thereof; most desirably, each X is independently alkoxy). It will be appreciated that the X groups will hydrolyze in the presence of water or moisture, and some portion of the X groups may be hydrolyzed to —OH groups, which may then form siloxane linkages with each other or with hydroxyl-containing substrate surface via dehydration condensation reactions.

The preferred hydrosilane of the formula VII is selected from H—$SiCl_3$, H—$Si(OMe)_3$ and H—$Si(OCH_2CH_3)_3$.

The fluoroalkyl silicones of Formula VIII may be prepared by hydrosilation with a hydrosilicone of the formula:

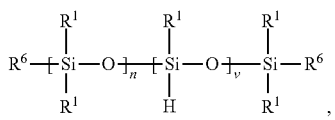

where
each $R^1$ is independently an alkyl or aryl;
n is 0 to 2000; preferably at least 10;
v may be zero;
$R^6$ is H, alkyl or aryl;
with the proviso that the hydrosilicone contains at least one Si—H group, preferably at least two Si—H groups. Thus the silicone unit with the subscript "v" of Formula III may be at least one, preferably at least 2, and/or $R^6$ can be H.

Examples of useful Si—H group containing silicones of Formula IX include hydride terminated polydimethylsiloxanes having the formula $HMe_2SiO(SiMe_2O)_nSiMe_2H$ (CAS 70900-21-9); hydride terminated methylhydrosiloxane-dimethylsiloxane copolymers having the formula $HMe_2SiO(SiMe_2O)_n(SiMeHO)_qSiMe_2H$ (CAS 69013-23-6); trimethylsiloxane terminated polyethylhydrosiloxanes having the formula $Me_3SiO(SiMeHO)_qSiMe_3$ (CAS 63148-57-2); trimethylsiloxane terminated methylhydrosiloxane-dimethylsiloxane copolymers having the formula $Me_3SiO(SiMe_2O)_n(SiMeHO)_qSiMe_3$ (CAS 68037-59-2); triethylsiloxane terminated polyethylhydrosiloxanes having the formula $Et_3SiO(SiEtHO)_qSiEt_3$ (CAS 24979-95-1); hydride terminated poly(phenyl-dimethylhydrosiloxysiloxanes) having the formula $HSiMe_2O(SiPh(OSiMe_2H)O)_qSiMe_2H$; all commercially available from vendors such as, for example, Gelest, Inc. or Dow Corning Corp. with different molecular weights.

All or a portion of the Si—H groups of the hydrosilicone may be reacted with the alkenyl ether of Formula I. In some embodiments, unreacted hydrosilyl (Si—H) groups may be converted to other useful functional groups, as described herein. In the presence of the hydrosilylation catalyst, the compounds of Formula I are hydrosilated by the hydrosilicone of Formulas VIII or IX to produce the fluoroalkyl silicones of Formulas V or X respectively. All or a portion of the Si—H groups may undergo the hydrosilylation with the compound of Formula I.

In the following Scheme I, subscript "v" represent the number of original in-chain hydrosilane units, m the number of those in-chain units substituted by hydrosilylation, and subscript s is the number of in-chain Si—H groups remaining. In addition, where $R^6$ is H, all or a portion of those terminal Si—H groups may undergo hydrosilylation to provide terminal $R_f$ groups in the $R^7$. In some embodiments, all of the Si—H groups, whether terminal or in-chain, will be converted to $-R^*-[OCF_2CHFOR_f]_x$ groups.

Scheme 1

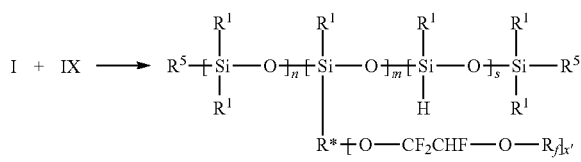

each R' is independently an alkyl or aryl;

$R_f$ is a perfluoroalkyl group, as previously described;
$R^3$ is —H, —$OR^4$; where $R^4$ is a $C_1$-$C_4$ alkyl
n is 0 to 2000;
m may be zero;
s may be zero;
n+m+p is at least one;
$R^5$ is H, alkyl, aryl —$R^*[-O-CF_2CHF-O-R_f]_x$, or $R^3$;
$R^*$ is a (hetero)hydrocarbyl groups of valence x+1;
x is at least 2;
wherein the fluoroalkyl silicone has at least one fluorinated group of the formula —$R^*$ [—O—$CF_2CHF$—O—$R_f]_x$.

Alternatively, the fluoroalkyl silicones of the formula VI can be made by condensation of the fluorlkylsilane of Formula V with one or more dihydrocarbydialkoxysilanes, such as dimethyldimethoxysilane.

Regarding the product of Formula X of Scheme I, the Si—H functional fluoroalkyl silicones may be used as a crosslinking agent, such as to thermally crosslink with silicones or fluorinated silicones having a plurality of ethylenically unsaturated bonds in a subsequent hydrosilylation reaction. In some embodiments, the fluoroalkyl silicone may be subsequently crosslinked by vinyl substituted silicones: i.e. silicone having a plurality of vinyl groups.

The non-fluorinated organopolysiloxane polymers (vinyl silicones) comprising an average of at least two ethylenically unsaturated organic groups may be formulated with the fluoroalkyl silicone of Formula V. In some embodiments, the non-fluorinated organopolysiloxane polymer has a vinyl equivalent weight of no greater than 60,000 grams per equivalent, e.g., no greater than 20,000, or even no greater than 10,000 grams per equivalent. In some embodiments, the non-fluorinated organopolysiloxane polymer has a vinyl equivalent weight of 2000 to 5000 grams per equivalent, e.g., 2000 to 4000 grams per equivalent, or even 2500 to 3500 grams per equivalent.

Exemplary non-fluorinated organopolysiloxane polymers include those comprising a triorganosiloxy end blocked polydiorganosiloxane polymer. In some embodiments, the non-fluorinated organopolysiloxane polymer comprises $R_2SiO_{2/2}$ units (i.e., "D" units) and $R_3SiO_{1/2}$ units (i.e., "M" units), wherein each R group independently represents a saturated or ethylenically unsaturated, substituted or unsubstituted hydrocarbon radical, provided that at least two R groups contain terminal ethylenic unsaturation.

The ethylenically unsaturated radicals are independently selected from the group consisting of the vinyl radical and higher alkenyl radicals represented by the formula —R'—CH=CH wherein R' denotes —$(CH_2)_w$—; and w has the value of 1-48.

In some embodiments, trace amounts of non-linear siloxane units, i.e., $SiO_{4/2}$ units (i.e., "Q" units) and $RSiO_{3/2}$, units (i.e., "T" units); may be present wherein R is as described above. In some embodiments, trace amounts of other silicon-bonded radicals, such as hydroxyl and alkoxyl may also be present.

Exemplary non-fluorinated organopolysiloxane polymer comprising an average of at least two ethylenically unsaturated organic groups include those having the formula $M^{vi}D_xM^{vi}$, wherein M represents M units, D represents D units, the superscript "vi" indicates the presence of vinyl-functional groups, and x is the degree of polymerization. Commercially available $M^{vi}D_xM^{vi}$, non-fluorinated organopolysiloxane polymers include those available under the trade designations DMS-V from Gelest Inc. (e.g., DMS-V03, DMS-V05, DMS-V21, DMS-V22, DMS-V25, DMS-V35, and DMS-V41).

Examples of useful silicone having a plurality of vinyl groups include vinyl terminated polydimethylsiloxanes having the formula $H_2C=CHSiMe_2O(SiMe_2O)_nSiMe_2CH=CH_2$ (CAS 68083-19-2); vinyl terminated dimethylsiloxane-diphenylsiloxane copolymers having the formula $H_2C=CHSiMe_2O(SiMe_2O)_n(SiPh_2O)_mSiMe_2CH=CH_2$ (CAS: 68951-96-2); vinyl terminated polyphenylmethylsiloxanes having the formula $H_2C=CHSiMePhO(SiMePhO)_nSiMePhCH=CH_2$ (CAS: 225927-21-9); vinyl-phenylmethyl terminated vinylphenylsiloxane-methylphenylsiloxane copolymers (CAS: 8027-82-1); vinyl terminated trifluoropropylmethylsiloxane-dimethylsiloxane copolymers having the formula $H_2C=CHSiMePhO(SiMe_2O)_n(SiMe(CH_2CH_2CF_3)O)_mSiMePhCH=CH_2$ (CAS: 68951-98-4); $H_2C=CHSiMe_2O-(SiMe_2O)_n(SiMe(CH_2CH_2CF_3)O)_m SiMe_2CH=CH_2$, $H_2C=CHSiMe_2O-(SiMe_2O)_n(SiMe(CH_2CH_2C_4F_9)O)_mSiMe_2CH=CH_2$, vinyl terminated dimethylsiloxane-diethylsiloxane copolymers having the formula $H_2C=CHSiMe_2O(SiMe_2O)_n(SiEt_2O)_nSiMe_2CH=CH_2$; trimethylsiloxy terminated vinylmethylsiloxane-dimethylsiloxane copolymers $Me_3SiO(SiMe_2O)_n(SiMe(CH=CH_2)O)_mSiMe_3$ (CAS: 67762-94-1); vinyl terminated vinylmethylsiloxane-dimethylsiloxane copolymers having the formula $H_2C=CH(SiMe_2O)_n(SiMeCH=CH_2O)_m SiMe_2CH=CH_2$ (CAS: 68063-18-1); vinylmethylsiloxane homopolymers (cyclic and linear) having the formula $Me_3SiO(SiMe(CH=CH_2)O)_nSiMe_3$; and vinyl T-structure polymers having the formula $MeSi[O(SiMe_2O)_m SiMe_2CH=CH_2]_3$; all commercially available from vendors such as, for example, Gelest, Inc., Morrisville, Pa. or Dow Corning Corp., Midland, Mich. Additional useful silicones having a plurality of vinyl groups include a vinyl-terminated fluorosilicone that is commercially available under the trade designations "SYL-OFF Q2-7785" and "SYL-OFF Q2-7786" from Dow Corning Corp.

In some embodiments, the Si—H group of Formula X, Scheme 1 may be converted to alkyl groups by subsequent hydrosilylation of an olefin of the formula: $CH_2=CHCH_2—R^4$, where $R^4$ is H or $C_1$-$C_{50}$ alkyl in the presence of a hydrosilylation catalyst.

Again with regard to the silicone of Formula IX, Scheme I, the Si—H groups may be converted to alkoxide groups (Si—H→Si—OR$^4$) and the alkoxy-functional fluoroalkyl silicone can be subsequently hydrolysis-condensation crosslinked by siloxane formation. Generally, the hydrides are reacted with an alcohol of the formula $R^4$—OH to convert all or a portion of the Si—H groups to Si—OR$^4$ groups, where $R^4$ is a $C_1$-$C_{50}$ alkyl, preferably a short alkyl group ($C_1$-$C_{16}$, preferably $C_1$-$C_4$) for easy hydrolysis. Thus the present disclosure provides crosslinkable, fluoroalkyl silicones of the formula:

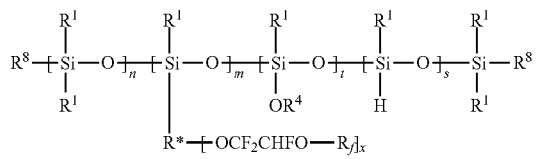

XI wherein
n is 0 to 2000;
m may be zero, preferably at least one;
s may be zero;
t may be zero, preferably at least one;

$R^8$ is H, alkyl or aryl, —R*—[OCF$_2$CHFOR$_f$]$_x$ or OR$^4$, where $R^4$ is $C_1$-$C_{50}$ alkyl;
x is at least 2; and
$R_f$ is a perfluoroalkyl group, as previously defined;
with the proviso that the silicone contains at least one, preferably at least two Si—OR$^4$ groups and the silicone contains at least one —R*[—O—CF$_2$CHF—O—R$_f$]$_x$ group.

In Formula XI, the unit with the subscript t may be at least one, preferably at least two, and/or $R^8$ may be —OR$^4$. Further, if only a portion of the Si—H groups are converted to alkoxysilane groups (Si—OR$^4$), then s may be at least one, and/or a portion of $R^8$ may be H. Further, the unit with the subscript m may be at least one, and/or a portion of the $R^8$ groups may be —R*[—O—CF$_2$CHF—O—R$_f$]$_x$. In some embodiments $R^4$ is lower-chain alkyl ($C_1$-$C_{16}$, preferably $C_1$-$C_4$). In other embodiments $R^4$ is long-chain alkyl ($C_{18}$-$C_{50}$)

Subsequently, these alkoxide groups (Si—OR$^4$) may be hydrolyzed by moisture, then crosslinked by dehydration, which can be catalyzed by a acid, or acid from a photoacid generator (PAG) initiated by photo irradiation, or a thermal acid generator initiated by heating to form siloxane Si—O—Si crosslinked polymers. The acid generator is preferably free of amines or ammonium compounds. The crosslinking of the alkoxide substituted silicones by photo irradiation in the presence of PAG is described in U.S. Pat. No. 6,129,980 or WO 9840439 (Liu et al.), incorporated herein by reference.

The conversion of all or a portion of the Si—H groups in the silicone to alkoxide groups by reacting the hydropolysiloxane with an alcohol in the presence of at least one of a Pd(0) and Pt(0) catalyst according to the methods of U.S. 2013074130 (Rathore et al.) and incorporated herein by reference.

A wide variety of acid generating materials can be used in the practice of the invention to catalyze the moisture curing reaction, including onium salts such as sulfonium and iodonium salts. Activating the acid generating material liberates an acid that initiates and accelerates crosslinking of the moisture-curable composition through the formation of Si—O—Si crosslinks. Activation may be accomplished by irradiating the composition with, for example, ultraviolet, visible light, electron beam or microwave radiation. While heat may be used to activate the acid generating material, the compositions of the invention advantageously do not require this and thereby can avoid undesirable damage to heat sensitive substrates.

Although the acid generating material described above is preferred due to the controlled curability it provides, it has been found that condensation catalysts, such as strong organic acids, weak Lewis acids, weak organic bases and metal chelates can also be used in the preparation of the novel silicone pressure-sensitive adhesive. Another preferred class of condensation catalyst is the strong organic acids having pKa values of less than about 3 and the anhydrides and ammonium salts thereof described in U.S. Pat. No. 5,286,815. Examples of useful strong organic acids and derivatives include trichloroacetic acid, cyanoacetic acid, malonic acid, nitroacetic acid, dichloroacetic acid, difluoroacetic acid, trichloroacetic anhydride, dichloroacetic anhydride, difluoroacetic arthydride, triethylammonium trichloroacetate, trimethylammonium trichloroacetate, and mixtures thereof.

The condensation catalyst or an acid generating material is used in amounts of about 0.5 to about 20 parts by weight, based on 100 parts by weight of the alkoxy functional silicone.

The fluoroalkyl silicone of Formula XI contains both Si—OR$^4$ and Si—H functional groups are dual curable, which may be controllably cured initially via Si—H with a vinyl silicone, then moisture or photo-acid cured from Si—OR$^4$ or vice versa.

The fluoroalkyl silicones of the Formulas have a $M_w$ of at least 400, preferably at least 1000. In some embodiments, the $M_w$ may be 2000 or greater. In some embodiments, the $M_w$ may be limited to 1,000,000 or less; preferably limited to 500,000 or less. In some embodiments n, m and p are each greater than one and where the ratio of n to m is greater than one, preferably the ratio of n to m is greater than 10. In some embodiments, $R^3$ is H, and the ratio of m to p is from 100:0 to 5:95. In some embodiments, $R^3$ is OR$^4$ (prepared as described herein).

Regarding the hydrosilation reaction, numerous patents teach the use of various complexes of cobalt, rhodium, nickel, palladium, or platinum as catalysts for hydrosilylation between a compound containing silicon-bonded hydrogen such as formula III and a compound containing terminal aliphatic unsaturation. For example, U.S. Pat. No. 4,288,345 (Ashby et al) discloses as a catalyst for hydrosilylation reactions a platinum-siloxane complex. Additional platinum-siloxane complexes are disclosed as catalysts for hydrosilylation reactions in U.S. Pat. Nos. 3,715,334, 3,775, 452, and 3,814,730 (Karstedt et al). U.S. Pat. No. 3,470,225 (Knorre et al) discloses production of organic silicon compounds by addition of a compound containing silicon-bonded hydrogen to organic compounds containing at least one non-aromatic double or triple carbon-to-carbon bond using a platinum compound of the empirical formula PtX$_2$(RCOCR'COR")$_2$ wherein X is halogen, R is alkyl, R' is hydrogen or alkyl, and R" is alkyl or alkoxy.

The catalysts disclosed in the foregoing patents are characterized by their high catalytic activity. Other platinum complexes for accelerating the aforementioned thermally-activated addition reaction include: a platinacyclobutane complex having the formula (PtCl$_2$C$_3$H$_6$)$_2$ (U.S. Pat. No. 3,159,662, Ashby); a complex of a platinous salt and an olefin (U.S. Pat. No. 3,178,464, Pierpoint); a platinum-containing complex prepared by reacting chloroplatinic acid with an alcohol, ether, aldehyde, or mixtures thereof (U.S. Pat. No. 3,220,972, Lamoreaux); a platinum compound selected from trimethylplatinum iodide and hexamethyldiplatinum (U.S. Pat. No. 3,313,773, Lamoreaux); a hydrocarbyl or halohydrocarbyl nitrile-platinum (II) halide complex (U.S. Pat. No. 3,410,886, Joy); a hexamethyldipyridine-diplatinum iodide (U.S. Pat. No. 3,567,755, Seyfried et al); a platinum curing catalyst obtained from the reaction of chloroplatinic acid and a ketone having up to 15 carbon atoms (U.S. Pat. No. 3,814,731, Nitzsche et al); a platinum compound having the general formula (R')PtX$_2$ where R' is a cyclic hydrocarbon radical or substituted cyclic hydrocarbon radical having two aliphatic carbon-carbon double bonds, and X is a halogen or alkyl radical (U.S. Pat. No. 4,276,252, Kreis et al); platinum alkyne complexes (U.S. Pat. No. 4,603,215, Chandra et al.); platinum alkenyl-cyclohexene complexes (U.S. Pat. No. 4,699,813, Cavezzan); and a colloidal hydrosilylation catalyst provided by the reaction between a silicon hydride or a siloxane hydride and a platinum (0) or platinum (II) complex (U.S. Pat. No. 4,705,765, Lewis).

Although these platinum complexes and many others are useful as catalysts in processes for accelerating the hydrosilation, processes for promoting the ultraviolet or visible radiation-activated addition reaction between these compounds may be preferable in some instances. Platinum complexes that can be used to initiate ultraviolet radiation-activated hydrosilation reactions have been disclosed, e.g., platinum azo complexes (U.S. Pat. No. 4,670,531, Eckberg); ($\eta^4$-cyclooctadiene)diarylplatinum complexes (U.S. Pat. No. 4,530,879, Drahnak); and ($\eta^5$-cyclopentadienyl)trialkylplatinum complexes (U.S. Pat. No. 4,510,094, Drahnak). Other compositions that are curable by ultraviolet radiation include those described in U.S. Pat. Nos. 4,640,939 and 4,712,092 and in European Patent Application No. 0238033. U.S. Pat. No. 4,916,169 (Boardman et al) describes hydrosilylation reactions activated by visible radiation. U.S. Pat. No. 6,376,569 (Oxman et al.) describes a process for the actinic radiation-activated addition reaction of a compound containing silicon-bonded hydrogen with a compound containing aliphatic unsaturation, said addition being referred to as hydrosilylation, the improvement comprising using, as a platinum hydrosilylation catalyst, an ($\eta^5$-cyclopentadienyl)tri($\sigma$-aliphatic)platinum complex, and, as a reaction accelerator, a free-radical photoinitiator capable of absorbing actinic radiation, i.e., light having a wavelength ranging from about 200 nm to about 800 nm. The process can also employ, as a sensitizer, a compound that absorbs actinic radiation, and that is capable of transferring energy to the aforementioned platinum complex or platinum complex/free-radical photoinitiator combination, such that the hydrosilylation reaction is initiated upon exposure to actinic radiation. The process is applicable both to the synthesis of low molecular weight compounds and to the curing of high molecular weight compounds, i.e., polymers.

This disclosure further provides coating composition comprising the fluoroalkyl silicon compounds in a solvent. Generally, the coating is formulated in a solvent or mixed solvents for easy use at the concentration of 0.01 to 50 wt %; preferably at 0.1 to 20%.

For crosslink or curing of the coating, moisture is needed, either by addition of limited water to the coating formulation or absorption of moisture from air after coating on substrates. To accelerate the curing, a acid or base catalyst may be optionally presented in the formulation.

In some embodiments, the coating composition may further comprise a crosslinking agent for the fluoroalkylsilane. A class of useful crosslinkers includes compounds that can be represented by the following general formula:

$$Si(X^1)_z R^{12}_{4-z} \qquad \text{XII}$$

wherein each $X^1$ is independently hydroxyl, a hydrolyzable group, or a combination thereof; each $R^{12}$ is independently a C$_1$-C$_4$ alkyl group; z is an integer of 1, 2, 3 or 4. Preferences for $X^1$ and $R^{12}$ include those set forth above for the X and R groups of Formulas V and VIII. The crosslinkers can be included in the surface treatment composition in any of a wide range of amounts (for example, from about 1 to 20 weight percent), depending, for example, upon the particular application and the desired properties. Most preferred are tetralkoxysilanes, such as commercial available tetraethoxysilane, alone or in a mixture with trialkoxysilanes.

A variety of non-functional inorganic oxide particulate solutions or dispersions can be used in the coating composition. The particles are typically substantially spherical in shape and relatively uniform in size. The particles can have a substantially monodisperse size distribution or a polymodal distribution obtained by blending two or more substantially monodisperse distributions. The inorganic oxide particles are typically non-aggregated (substantially discrete), as aggregation can result in precipitation of the inorganic oxide particles or gelation of the composition.

The inorganic oxide particles are typically colloidal, having an average particle diameter of about 0.001 to about 0.2 micrometers, less than about 0.05 micrometers, and less than about 0.03 micrometers. These size ranges facilitate dispersion of the inorganic oxide particles into the coating composition with desirable surface properties and optical clarity. The average particle size of the inorganic oxide particles can be measured using transmission electron microscopy to count the number of inorganic oxide particles of a given diameter.

Inorganic oxide particles include colloidal silica, colloidal titania, colloidal alumina, colloidal zirconia, colloidal vanadia, colloidal chromia, colloidal iron oxide, colloidal antimony oxide, colloidal tin oxide, and mixtures thereof. The inorganic oxide particles can consist essentially of or consist of a single oxide such as silica, or can comprise a combination of oxides, such as silica and aluminum oxide, or a core of an oxide of one type (or a core of a material other than a metal oxide) on which is deposited an oxide of another type. Silica is a common inorganic particle for general applications.

The inorganic oxide particles are often provided in the form of a sol containing a colloidal dispersion of inorganic oxide particles in liquid media including water and isopropanol as solvent. The sol can be prepared using a variety of techniques and in a variety of forms including hydrosols (where water serves as the liquid medium), organosols (where organic liquids so serve), and mixed sols (where the liquid medium contains both water and an organic liquid), e.g., as described in U.S. Pat. No. 5,648,407 (Goetz et al.); U.S. Pat. No. 5,677,050 (Bilkadi et al.) and U.S. Pat. No. 6,299,799 (Craig et al.), the disclosure of which is incorporated by reference herein. Aqueous sols (e.g. of amorphous silica) can be employed. Sols generally contain at least 2 wt-%, at least 10 wt-%, at least 15 wt-%, at least 25 wt-%, and often at least 35 wt-% colloidal inorganic oxide particles based on the total weight of the fluorosilane in the coating formulation. The amount of colloidal inorganic oxide particle is typically no more than 50 wt-%. Most water is generally removed from the aqueous sols prior to formulating with fluorosilane to prevent premature hydrolysis for sufficient shelf life stability.

The coating composition can be prepared by mixing the inorganic oxide particle solution, and other optional ingredients with the curable fluorosilane composition. The resulting composition after applied to a substrate usually is dried to remove substantially all of the solvent and/or water from the formulation or generated during the silanol dehydration condensation reaction.

Some embodiments, partially surface-modified inorganic particles, preferably nanoparticles (having an average particle size of less than 100 nanometers) may be used. These particles and nanoparticles are prepared from colloidal materials from the group of silica, zinc oxide, titania, alumina, zirconia, vanadia, chromia, iron oxide, antimony oxide, tin oxide, other colloidal metal oxides, and mixtures thereof, modified such that the particles can be easily formulated or dispersed with fluorosilane formulation; these particles can comprise essentially a single oxide such as silica or can comprise a core of an oxide of one type (or a core of a material) on which is deposited the oxide of another type. The particles have an average particle diameter of 5 to about 1000 nm, preferably less than 100 nanometers, more preferably 10 to 50 nm. Average particle size can be measured using transmission electron microscopy to count the number of particles of a given diameter. Additional examples of suitable colloidal silicas are described in U.S. Pat. No. 5,126,394, incorporated herein by reference. Such particles are described in U.S. Pat. Nos. 6,353,037, and 6,462,100 (Thunhorst et al.), and U.S. Pat. No. 6,329,058 (Arney et al.) and are incorporated herein by reference. The fluorosilane of formula I may also been used for partial modification of inorganic particles.

The resulting curable coating composition can have a relatively long shelf life in the absence of moisture. The components of the composition can be in the form of relatively viscous liquids that can be used in the surface treatment process of the invention in neat form or, preferably, in admixture with commonly-used solvents (for example, alkyl esters, ketones, alkanes, alcohols, and the like, and mixtures thereof).

In some embodiments, the coating composition further includes at least one organic solvent that can dissolve or suspend at least about 0.1 percent by weight of the fluoroalkylsilane of Formulas V and VI and silicate components of Formula XII, based upon the total weight of the surface treatment composition. In some embodiments, it can be desirable that the solvent or mixture of solvents have a solubility for water of at least about 1 percent by weight, and for certain of these embodiments, a solubility for acid of at least about 5 percent by weight. When solvent is used, useful concentrations of the components can vary over a wide range (for example, from about 0.01 or 0.1 or 1 to about 90 weight percent), depending upon the solubility of the components, the application method utilized, the nature of the substrate, and the desired surface treatment characteristics.

Suitable organic solvents for use in the surface treatment composition include aliphatic alcohols such as, for example, methanol, ethanol, and isopropanol; ketones such as acetone and methyl ethyl ketone; esters such as ethyl acetate and methyl formate; ethers such as diethyl ether, diisopropyl ether, methyl t-butyl ether, and dipropylene glycol monomethyl ether (DPM); hydrocarbons solvents such as alkanes, for example, heptane, decane, and other paraffinic solvents; perfluorinated hydrocarbons such as perfluorohexane and perfluorooctane; fluorinated hydrocarbons, such as pentafluorobutane; hydrofluoroethers such as methyl perfluorobutyl ether and ethyl perfluorobutyl ether; and the like; and combinations thereof. Preferred solvents include aliphatic alcohols, perfluorinated hydrocarbons, fluorinated hydrocarbons, hydrofluoroethers, and combinations thereof (more preferably, aliphatic alcohols, hydrofluoroethers, and combinations thereof; most preferably, hydrofluoroethers and combinations thereof).

The coating composition may comprise:
a) 0.25 to 10 wt. % fluoroalkylsilane of Formulas V or VI;
b) 0 to 20 wt. % inorganic particulate filler;
c) 0 to 20 wt. % a silane crosslinker of Formula XII;
d) 0 to 10 wt. % of an acid catalyst;
in an organic solvent.

The coating composition can be used as a fluorochemical surface treatment to impart a degree of hydrophobicity and/or oleophobicity to a variety of substrates. Substrates suitable for use in the process of the invention (and for preparing the surface-treated articles of the invention) include those having at least one surface comprising a material that is solid and preferably substantially inert to any coating solvent that is used. Preferably, the surface treatment can adhere to the substrate surface through chemical interactions, physical interactions, or a combination thereof (more preferably, a combination thereof).

Suitable substrates can comprise a single material or a combination of different materials and can be homogeneous or heterogeneous in nature. Useful heterogeneous substrates include coated substrates comprising a coating of a material (for example, a glass or a primer) borne on a physical support (for example, a polymeric film).

Useful substrates include those that comprise wood, glass, minerals (for example, both man-made ceramics such as concrete and naturally-occurring stones such as marble and the like), polymers (for example, polycarbonate, polyester, polyacrylate, and the like), metals (for example, copper, silver, aluminum, iron, chromium, stainless steel, nickel, and the like), metal alloys, metal compounds (for example, metal oxides and the like), leather, parchment, paper, textiles, painted surfaces, and combinations thereof. Preferred substrates include those having siliceous surfaces in either primed or unprimed form. Preferred substrates include glass, minerals, wood, metals, metal alloys, metal compounds, primed polymers, and combinations thereof (more preferably, glass, minerals, metals, metal alloys, metal compounds, primed polymers, and combinations thereof; most preferably, glass, minerals, and combinations thereof).

Typically the substrate will be chosen based in part on the desired optical and mechanical properties for the intended use. Such mechanical properties typically will include flexibility, dimensional stability and impact resistance. The substrate thickness typically also will depend on the intended use. For most applications, substrate thicknesses of less than about 0.5 mm are preferred, and more preferably about 0.02 to about 0.2 mm. Self-supporting polymeric films are preferred. The polymeric material can be formed into a film using conventional filmmaking techniques such as by extrusion and optional uniaxial or biaxial orientation of the extruded film. The substrate can be treated to improve adhesion between the substrate and the coating layer, e.g., chemical treatment, corona treatment such as air or nitrogen corona, plasma, flame, or actinic radiation. If desired, an optional tie layer or primer can be applied to the substrate and/or coating layer to increase the interlayer adhesion.

For best efficacy, the substrate has a surface with groups capable of forming covalent bonds to the silane groups (for example, hydroxyl groups). In some embodiments, the suitability of the surface of the substrate can be improved by deposition of a primer or by some other physical or chemical surface modification technique. Plasma deposition techniques can be used, if desired.

The coating composition can be applied separately or in combination (preferably, in combination) to at least a portion of at least one major surface of the substrate in essentially any manner (and with essentially any thickness) that can form a useful coating. Useful application methods include coating methods such as dip coating, spin coating, spray coating, wiping, roll coating, brushing, spreading, flow coating, and the like, and combinations thereof.

Typically, the coating composition can be coated on the substrate such that after an optional drying, a monolayer of the surface treatment composition results. Typically, such a monolayer can be from about 0.001 to about 1 micrometer thick (more typically, from about 0.001 to about 0.10 microns thick).

After application to the substrate, the coating can be cured by exposure to heat and/or moisture. Moisture cure can be effected at temperatures ranging from room temperature (for example, about 20° C.) up to about 80° C. or more. Moisture curing times can range from a few minutes (for example, at the higher temperatures) to hours (for example, at the lower temperatures).

For the preparation of a durable coating, sufficient water typically can be present to cause hydrolysis of the hydrolyzable groups described above, so that condensation to form siloxane (Si—O—Si) groups between the fluoroalkylsilanes of Formula I and also the substrate. The water can be, for example, present in the coating composition, adsorbed on the substrate surface, or in the ambient atmosphere. Typically, sufficient water can be present for the preparation of a durable coating if the coating method is carried out at room temperature in an atmosphere containing water (for example, an atmosphere having a relative humidity of about 30 percent to about 50 percent). Preferably, the coating composition can undergo chemical reaction with the surface of the substrate to form a durable coating through the formation of covalent bonds (including Si—O—Si groups).

Useful moisture curing catalysts for silane compounds are well-known in the art and include organic or inorganic acids (for example, acetic acid, propionic acid, butyric acid, valeric acid, maleic acid, stearic acid, hydrochloric acid, nitric acid, sulfuric acid, phosphoric acid, hydrochloric acid, and the like, and combinations thereof), metal carboxylates, metal acetylacetonate complexes, metal powders, peroxides, metal chlorides, organometallic compounds, and the like, and combinations thereof.

When used, the acid catalysts can be present in amounts ranging from about 0.01 to about 10 weight percent (preferably, from about 0.25 to about 10 weight percent; more preferably, from about 0.25 to about 5 weight percent), based upon the total weight of catalyst and surface treatment composition).

A substrate to be coated can typically be contacted with the coating composition at room temperature (typically from 20° C. to 30°. Alternatively, the coating composition can be applied to substrates that are preheated at a temperature of, for example, between 60° C. and 150° C. Following application of the surface treatment composition, the coated substrate can be dried and the resulting coating cured at ambient temperature (for example, about 20° C. to about 30° C. or elevated temperature (for example, at about 40° C. to about 150° C.) for a time sufficient for the curing to take place.

Regarding the fluoroalkyl silanes of Formula V, the cured coating may be described by the general formula:

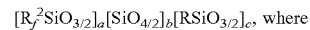

$[R_f^2SiO_{3/2}]_a[SiO_{4/2}]_b[RSiO_{3/2}]_c$, where $R_f^2$ is $[R_f$—O—CHFCF$_2$—O-$]_xR^*$- and the unit is derived from the fluoroalkylsilane of Formula V where subscript "q" is 3,

[SiO$_{4/2}$] are units derived from the tetraalkoxysilanes;

[RSiO$_{3/2}$] are units derived from the trialkoxysilanes. It will be appreciated that some siloxane bond formation will form with certain substrates.

The curable coating composition can be applied to articles comprising one or more of the above-described substrates and then cured to form surface treatments in the form of crosslinked hardcoats. The hardcoats can exhibit surface and/or bulk properties that can be tailored by varying the degree of crosslinking and by varying the natures and relative amounts of the particulate filler. The hardcoats (with their often outstanding durability, adhesion, and repellency properties) can be widely used for applications requiring durable low surface energy characteristics (for example, anti-graffiti coatings for signs, buildings, transportation vehicles, and the like; easily cleanable and/or anti-smudge coatings for glass, paper, clothes, metals, ceramic tiles, electronic devices, optical devices, and the like; mold release coatings for polymer or composite molding; and the like).

A useful hardcoat coating composition comprises:
a) 0.5 to 5 wt % fluoroalkylsilane of Formulas V or VI;
b) 1 to 10 wt % nanoparticle silica, and/or
c) 1 to 10 wt % silane crosslinker of Formula X.

In general, the method of coating comprises providing a substrate, coating at least a portion of the substrate with the coating composition, optionally drying to remove water and/or solvent, and curing the coating. The resulting coating articles are both oleo- and hydrophobic. In some embodiments the coating exhibits a having a receding water contact angle of at least 80°, or at least 90°.

Examples

Materials

| Designation | Description | Source |
|---|---|---|
| HDO | 5-Hexene-1,2-diol [$CH_2=CH(CH_2)_2CH(OH)CH_2OH$], 90% | Aldrich Chemical Company, Milwaukee, WI |
| ODO | 7-Octene-1,2-diol [$CH_2=CH(CH_2)_4CH(OH)CH_2OH$], 97% | |
| APDO | 3-Allyl-1,2-propanediol [$CH_2=CHCH_2OCH_2CH(OH)CH_2OH$], 99% | |
| TMPAE | Trimethylol propane allyl ether [$CH_2=CHCH_2OCH_2CEt(CH_2OH)_2$], 98% | |
| MG | 1,2-Dimethoxyethane | GFS Chemicals, Powell, OH |
| KOH | Potassium hydroxide, pellets | J. T. Baker, Center Valley, PA |
| MV-3 | $C_3F_7OCF=CF_2$ | VWR, Batavia, IL |
| MV-31 | $CF_3O(CF_2)_3OCF=CF_2$ | VWR, Batavia, IL |
| PPVE-2 | $C_3F_7OCF(CF_3)CF_2OCF=CF_2$ | Prepared as in Example 21 of U.S. Pat. No. 6,255,536 (Worm et al.) |

Test Methods
Method for High Resolution GC-MS (HR GC-MS) Analysis Method

The sample was dissolved in chloroform at 1 mg/mL concentration and the solution was used for analysis. High resolution accurate Gas Chromatography—Mass Spectrometry (GC-MS) analysis was carried out using an Agilent High Definition 7200 GC-QTOF instrument (from Agilent Technologies, Santa Clara, Calif.) equipped with GC 7890A system. The analyte molecules were ionized using both electron impact ionization (EI) and chemical ionization (CI). The sample components were separated using a 30 meter DB-5 ms capillary column (diameter: 250 μm, film thickness: 0.25 μm). The column temperature was programmed to increase from 40° C. to 320° C. at a linear rate of 15° C./min with a final hold time of 10 minutes. Helium was used as the carrier gas and the flow rate was set at 1.1 mL/min. 1 μL of sample solution was introduced into the GC/MS system. The injector temperature was 280° C. and was operated in split mode (split ratio 20:1 or 30:1).

General Procedure for Making Polyalkylated Alkenes

In a 200 ml Parr pressure reactor (form Parr Instrument Company, Moline, Ill.), 0.2 mol of ethylene-terminated (EPO), 30 g MG and 3.0 g KOH pellet were charged. Then, ~0.44 mol perfluorinated vinyl ether (PVE, excess) was added, and the reactor was sealed. Under stirring (~300 RPM), the mixture was heated to 70° C. and reacted for 24 hours. The pressure raised up to ~50 psi (344.7 kPa) before dropping and stabilizing at ~10 psi (68.9 kPa) from the excess PVE. The solution was poured out after cooling to room temperature. Distillation to recover MG and unreacted PVE. Then the residue was washed with 0.1N HCl aqueous solution, followed by two times washing with distilled water. The bottom layer product solution was isolated and dried over anhydrous $Na_2SO_4$. Distillation in full vacuum, isolated the product. All products were confirmed by the analyses of $^{19}F/^1H$ NMR and HR GC-MS spectra.

Examples 1-6 (EX1-EX6)

EX1-EX6 samples were prepared by using the general procedure for making polyalkylated alkenes described above. Table 1, below summarizes the reactants, yield and boiling points of products of each EX1-EX6. The structure and HR-GCMS analysis results are summarized in Table 2, below.

TABLE 1

| Example | Polyol | Perfluorovinyl ether | Yield (%)* | Boiling Point |
|---|---|---|---|---|
| EX1 | HDO | PPVE-2 | 81.38 | 122-125° C./ 319.97 Pa |
| EX2 | HDO | MV-3 | 88.5 | 113.5-115° C./ 1.93 kPa |
| EX3 | ODO | MV-3 | 85.2 | 101-104° C./ 693.28 Pa |
| EX4 | APDO | MV-3 | 87.8 | 98-100° C./ 333.31 Pa |
| EX5 | TMPAE | MV-3 | 70.2 | 106-108.5° C./ 346.64 Pa |
| EX6 | ODO | MV-31 | 90.1 | 115-120° C./ 519.96 Pa |

*isolated yields based on EPO.

TABLE 2

| Example | Structure | HRMS (Expected) |
|---|---|---|
| EX1 | $CH_2=CH(CH_2)_2CHCH_2OCF_2CHFOCF_2CF(CF_3)OC_3F_7$-r with branch $OCF_2CHFOCF_2CF(CF_3)OC_3F_7$-n | C22 H12 F32 O6, 998.0528 (998.0461) |
| EX2 | $CH_2=CH(CH_2)_2CHCH_2OCF_2CHFOC_3F_7$-n with branch $OCF_2CHFOC_3F_7$-n | C16 H12 F20 O4 666.0754 (666.0750) |
| EX3 | $CH_2=CH(CH_2)_4CHCH_2OCF_2CHFOC_3F_7$-n with branch $OCF_2CHFOC_3F_7$-n | C18 H16 F20 O4 694.1065 (694.1067) |

TABLE 2-continued

| Example | Structure | HRMS (Expected) |
|---|---|---|
| EX4 | CH$_2$=CHCH$_2$OCH$_2$CHCH$_2$OCF$_2$CHFOC$_3$F$_7$-n<br>\|<br>OCF2CHFOC3F7-n | C16 H12 F20 O5<br>682.0693 (682.0704) |
| EX5 | CH$_2$=CHCH$_2$OCH$_2$CCH$_2$OCF$_2$CHFOC$_3$F$_7$-n<br>\|<br>CH2OCF2CHFOC3F7-n<br>\|<br>CH$_2$CH$_3$ | C19 H18F20 O5<br>724.1171 (724.1173) |
| EX6 | CH$_2$=CH(CH$_2$)$_4$CHCH$_2$OCF$_2$CHFOC$_3$F$_6$OCF$_3$<br>\|<br>OCF$_2$CHFOC$_3$F$_6$OCF$_3$ | C20 H16 F24 O6<br>826.0919 (829.0902) |

What is claimed:

1. A polyfluoralkylated alkene of the formula:

[R$_f$—O—CHFCF$_2$—O]$_x$—R*—CH=CH$_2$, wherein

R$_f$ is a perfluoroalkyl group, optionally substituted by one or more in-chain —O—, —S— or —NR$_f^1$— heteroatoms, where R$_f^1$ is a perfluoroalkyl;
subscript x is two;
R* is a C$_2$-C$_{10}$ alkylene group.

2. The alkene of claim 1 wherein R$_f$ is a C$_1$-C$_6$ perfluorolkyl group.

3. The alkene of claim 1, wherein R$_f$ is selected from —CF$_3$, —CF$_2$CF$_3$, —C$_3$F$_7$, —C$_4$F$_9$, —C$_5$F$_{11}$, —C$_6$F$_{13}$, CF$_3$O(CF$_2$)$_2$CF$_2$—, (CF$_3$)$_2$N(CF$_2$)$_2$CF$_2$—, —CF$_2$CF(CF$_3$)$_2$ and C$_3$F$_7$OCF(CF$_3$)CF$_2$—.

4. The alkene of claim 1 wherein R$_f$ is of the formula C$_a$F$_{2a+1}$—(O—C$_b$F$_{2b}$)$_c$—, where each of subscripts a and b is a number from 3 to 6, and c is a number from 1 to 10.

5. The alkene of claim 1 wherein R$_f$ is of the formula C$_a$F$_{2a+1}$N(C$_a$F$_{2a+1}$)—C$_b$F$_{2b}$, where each of subscripts a and b is a number from 3 to 6.

* * * * *

UNITED STATES PATENT AND TRADEMARK OFFICE
CERTIFICATE OF CORRECTION

PATENT NO. : 9,975,834 B2
APPLICATION NO. : 15/324741
DATED : May 22, 2018
INVENTOR(S) : Qiu

Page 1 of 1

It is certified that error appears in the above-identified patent and that said Letters Patent is hereby corrected as shown below:

On the Title Page

Column 1,
Line 3, after "0 days." delete "days".

In the Specification

Column 5,
Line 67, delete "R'" and insert -- $R^1$ --, therefor.

Column 7,
Line 29, delete "CH=CH$_2$]$_3$;" and insert -- CH=CH$_2$]$_3$; --, therefor.

Column 10,
Line 50, delete "R'$^2$" and insert -- $R^{12}$ --, therefor.

Signed and Sealed this
Seventeenth Day of July, 2018

Andrei Iancu
*Director of the United States Patent and Trademark Office*